(12) United States Patent
Buiser et al.

(10) Patent No.: US 9,907,555 B2
(45) Date of Patent: Mar. 6, 2018

(54) GUIDED DETACHABLE INTERLOCK AND METHOD OF USE

(75) Inventors: Marcia Buiser, Marlborough, MA (US); Christopher Nardone, N. Chelmsford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1821 days.

(21) Appl. No.: 12/188,585

(22) Filed: Aug. 8, 2008

(65) Prior Publication Data

US 2009/0043331 A1    Feb. 12, 2009

Related U.S. Application Data

(60) Provisional application No. 60/954,883, filed on Aug. 9, 2007.

(51) Int. Cl.
*A61F 2/06* (2013.01)
*A61B 17/12* (2006.01)

(52) U.S. Cl.
CPC .... *A61B 17/12022* (2013.01); *A61B 17/1214* (2013.01); *A61B 2017/12054* (2013.01)

(58) Field of Classification Search
CPC .......... A61B 17/12022; A61B 17/1214; A61B 2017/12054
USPC ......................................... 623/1.11; 606/200
See application file for complete search history.

(56) References Cited

U.S. PATENT DOCUMENTS

| | | | | |
|---|---|---|---|---|
| 5,250,071 A | * | 10/1993 | Palermo | A45D 42/24 128/898 |
| 5,261,916 A | * | 11/1993 | Engelson | A61B 17/12022 604/171 |
| 5,304,195 A | * | 4/1994 | Twyford, Jr. | A61B 17/12022 604/907 |
| 5,853,375 A | * | 12/1998 | Orr | A61M 25/0905 600/585 |
| 5,895,385 A | | 4/1999 | Guglielmi et al. | |
| 5,925,059 A | * | 7/1999 | Palermo | A61B 17/12022 606/191 |

(Continued)

FOREIGN PATENT DOCUMENTS

| | | |
|---|---|---|
| EP | 0 829 236 A1 | 3/1998 |
| EP | 829236 A1 * | 3/1998 ............. A61B 17/12 |

(Continued)

OTHER PUBLICATIONS

Boston Scientific Corp. "Interlock™ Fibered IDC Occlusion System—Pioneering Precision" 2006 (2 pages).

(Continued)

*Primary Examiner* — Eric Rosen
*Assistant Examiner* — Son Dang

(57) ABSTRACT

Described herein are various implant delivery methods and systems that include a detachable link for connecting an implantable device and a control wire. The detachable link can include an elongate body comprising a first arm with a mating surface having a slot extending the width of the elongate body and a second arm having a mating surface that includes a extension portion adapted to mate with the slot. A guide member can extend between the first and second arms and inhibit relative transverse and/or rotational movement between the first and second arms.

19 Claims, 7 Drawing Sheets

(56) References Cited

U.S. PATENT DOCUMENTS

| | | | |
|---|---|---|---|
| 5,944,733 A * | 8/1999 | Engelson | A61B 17/12022 606/191 |
| RE37,117 E * | 3/2001 | Palermo | A61B 17/12022 128/898 |
| 2004/0199175 A1* | 10/2004 | Jaeger | A61B 17/12022 606/108 |
| 2005/0004598 A1 | 1/2005 | White, Jr. et al. | |
| 2007/0141099 A1 | 6/2007 | Buiser et al. | |
| 2007/0142859 A1 | 6/2007 | Buiser et al. | |
| 2007/0142893 A1 | 6/2007 | Buiser et al. | |
| 2007/0299461 A1* | 12/2007 | Elliott | A61B 17/12022 606/191 |

FOREIGN PATENT DOCUMENTS

| | | | |
|---|---|---|---|
| WO | WO 93/11719 A1 | 6/1993 | |
| WO | WO 93/11825 A1 | 6/1993 | |

OTHER PUBLICATIONS

Murphy, K.J. et al. "Mechanical Detachable Platinum Coil: Report of the European Phase II Clinical Trial in 60 Patients" *Radiology* 219:541-544 (2001).

Murphy, K.J. et al. "A Report of the Clinical Use of the Detach-18 Mechanical Detachable Platinum Coil in 41 Patients" *Am. J. Neuroradiol.* (*AJNR*) 22:341-344 (Feb. 2001).

\* cited by examiner

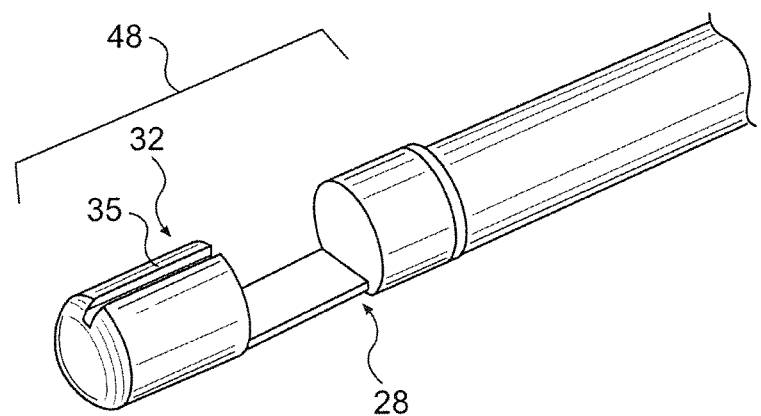
FIG. 2B
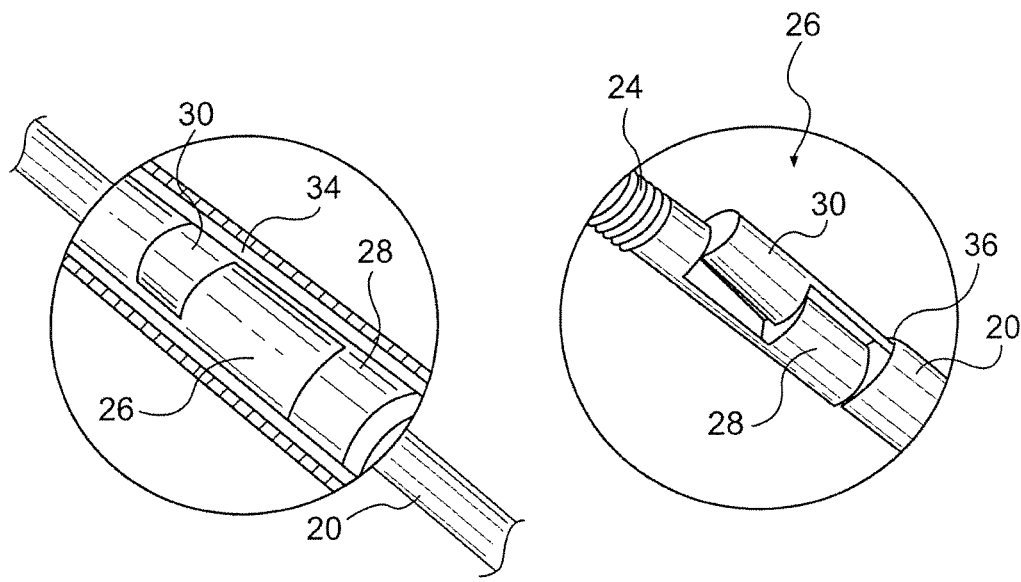
FIG. 3A     FIG. 3B

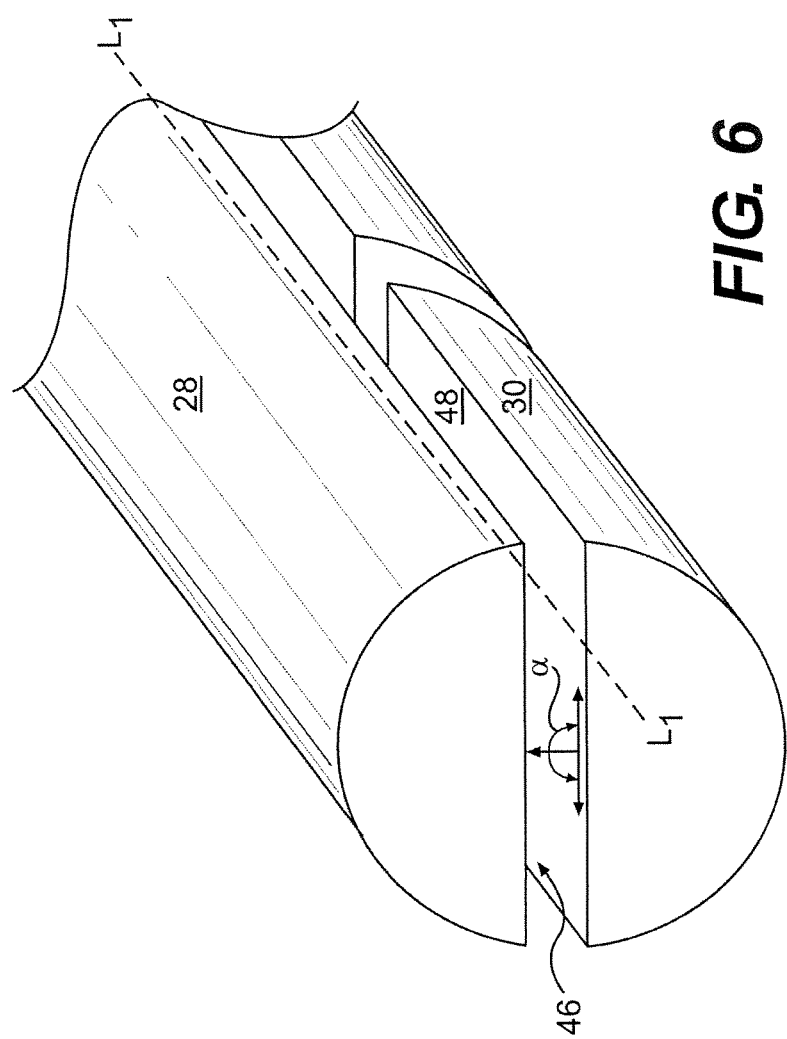

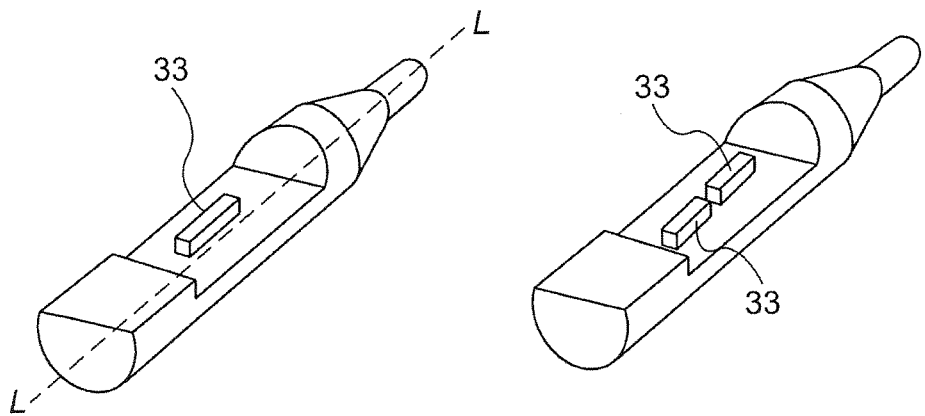
FIG. 9A          FIG. 9B
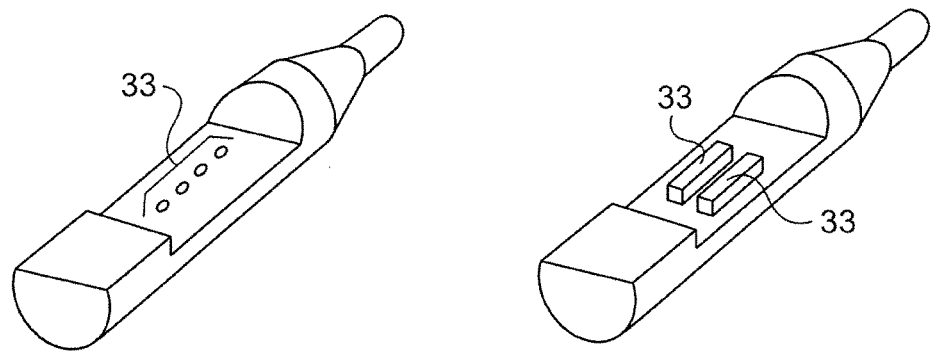
FIG. 9D          FIG. 9C
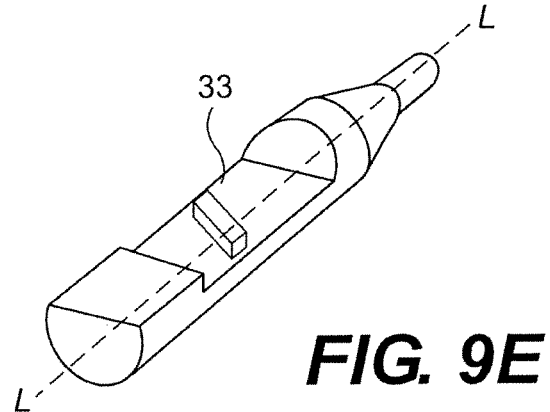
FIG. 9E

GUIDED DETACHABLE INTERLOCK AND METHOD OF USE

This application claims priority to U.S. Provisional Application No. 60/954,883, entitled "GUIDED DETACHABLE INTERLOCK AND METHOD OF USE," filed Aug. 9, 2007, which is incorporated by reference herein.

BACKGROUND OF THE INVENTION

The endovascular treatment of a variety of maladies throughout the body is an increasingly more important form of therapy. One such procedure uses embolizing coils to occlude a target site by posing a physical barrier to blood flow and/or by promoting thrombus formation at the site. Such treatments can be useful where it is desired to reduce vascularization, including treatments for aneurysms and cancer.

Coils have typically been placed at the desired site within the vasculature using a catheter and a pusher. As a first step, a flexible, small diameter catheter can be guided to the target site through the use of guidewires or by flow-directed means such as balloons placed at the distal end of the catheter. Once the site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site.

Several techniques have been developed to enable more accurate placement of coils within a vessel. In one technique the coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. In addition to enabling accurate coil placement, the electric current may facilitate thrombus formation at the coil site. A perceived disadvantage of this method is that the electrolytic release of the coil requires a period of time to allow the connection to degrade, and therefore, rapid detachment of the coil from the pusher does not occur.

Another technique for detaching an embolic coil uses a mechanical connection between the coil and the pusher. For example, one such device uses interlocking clasps which are secured to each other by a control wire that extends the length of the catheter. Retraction of the control wire uncouples the coil from the pusher. While mechanical connections between coils and pusher wires provide for quick detachment, such detachable coils require additional control mechanisms (i.e., control wires) to deploy the coil.

Accordingly, while conventional systems provide effective coil delivery, further improvements that reduce the chance of premature deployment or jamming would be beneficial.

SUMMARY OF THE INVENTION

Described herein are systems and methods for delivering a detachable, implantable device. In one embodiment, a system includes a detachable link connecting the implantable device to a pusher wire, wherein the detachable link self-detaches after exiting a catheter lumen. The detachable link can include a guide member that inhibits detachment of the detachable link during transit through the catheter. For example, the detachable link can include first and second engaging members and the guide member can reduce the movement between the first and second engaging members by at least one degree of freedom.

In one embodiment the detachable link can include an elongate body extending along a longitudinal axis from a proximal end to a distal end. The body comprising a first arm having a mating surface that includes a transverse slot extending the width of the elongate body and a second arm having a mating surface that includes a extension portion adapted to mate with the transverse slot.

The guide member can extend between the first and second arms, wherein the guide member is adapted to inhibit relative transverse and/or rotational movement between the first and second arms. For example, the guide member can prevent transverse movement of the extension portion within the slot when the first and second arms are mated.

In another aspect, the slot and extension portion can limit relative longitudinal movement of the first and second arms when the first and second arms are engaged and the guide member can limit relative transverse movement of the first and second arms when the first and second arms are engaged. In a further aspect, the slot and extension portion do not limit relative transverse movement of the first and second arms when the first and second arms are engaged.

In yet another aspect, the guide member reduces the freedom of relative movement between the first and second arms by more than one degree of freedom. For example, the guide member can limit relative transverse movement of the engaging members along at least one axis and can also limit relative pivotal movement of the engaging members.

In another aspect, the guide member includes a protrusion extending from the first arm and a corresponding recess in the second arm. The system can further include more than one protrusion and/or recess. The first and second arms can include a variety of shapes and sizes configured to provide a mechanical interlock.

In another embodiment, the implant delivery system comprises a catheter having an inner lumen and an implantable device and a control wire coupled via a detachable link. The detachable link can include a longitudinally extending body portion comprising first and second engaging members where the first and second engaging members each have an outer surface corresponding to at least a portion of the inner lumen of the catheter and an inner mating surface for mating with the other engaging member. The mating surfaces of the first and second engaging members can include an extension portion and a laterally extending channel. In one aspect, at least one of the mating surfaces further includes a guide protrusion extending from the laterally extending channel and a guide recess in the extension portion. The guide protrusion and guide recess are adapted to inhibit relative transverse movement of the first and second engaging members when the first and second engaging members are positioned within the catheter lumen.

In one aspect, the guide protrusion and guide recess extend longitudinally and are adapted to mechanically engage. In another aspect, the system includes multiple guide protrusions and guide recesses.

In another aspect, the outer shape of the first and second engaging members, when mated, substantially corresponds to the inner surface of the catheter lumen to inhibit radial separation of the first and second engaging members. The inner shapes of the first and second engaging members can include surfaces transverse to a longitudinal axis of the detachable link that permit transmission of longitudinal forces between the first and second engaging members when mated. In another aspect, the inner shapes of the first and second engaging members allow the detachable link to self-detach upon exiting the catheter.

In another embodiment, a method of delivering an implantable device is provided. The method can include the step of providing an implantable device connected to a control wire via a detachable link, the detachable link comprising an elongate body extending along a longitudinal axis from a proximal end to a distal end. The body can include a first arm having a mating surface that includes a transverse slot extending the width of the elongate body and a second arm having a mating surface that includes an extension portion corresponding to the transverse slot. A guide member can extend between the first and second arms. The method can further comprise the step of moving the implantable device through a catheter by pushing the control wire, wherein at least some of the forces transverse to the elongate body are transmitted between the first and second arms via the guide member. Delivery of the implantable device can be achieved by pushing at least a portion of the detachable link out of a distal end of the catheter such that the catheter no longer constrains the detachable link and allows detachable link to detach.

In one aspect, the method includes actuating the control wire, prior to the step of delivering, such that the detachable link partially exits the distal end of the catheter and then reenters the distal end without detaching. In another aspect, the method also includes the step of determining the location of the detachable link relative to the distal end of the catheter. For example, the location can be determined with a radiological technique such as, for example, x-ray, MRI, CT, PET, SPECT, fluoroscopy.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

FIG. 2B is a perspective view of another engaging member used with the system of FIG. 1;

FIG. 3A is a transparent view of a catheter illustrating an embodiment of the detachable link in a locked configuration;

FIG. 3B is a perspective view of the detachable link of FIG. 3A detaching after exiting the distal end of the catheter;

FIG. 6 is a cross-sectional view of a detachable link described herein;

FIG. 9A is a perspective view of an embodiment of the engaging member described herein;

FIG. 9B is a perspective view of another embodiment of the engaging member;

FIG. 9C is a perspective view of yet another embodiment of the engaging member;

FIG. 9D is a perspective view of still another embodiment of the engaging member;

FIG. 9D is a perspective view of another embodiment of the engaging member;

DETAILED DESCRIPTION

Disclosed herein are methods and systems for delivering an implantable device to a target site, particularly, a detachable, implantable device. The detachable, implantable device can be mated to a pusher wire via a detachable link that comprises first and second engaging members. Discussed below are a variety of detachable links which include features adapted to inhibit unwanted detachment during delivery of the implantable device through a catheter. In one embodiment, a guide member extends from a mating surface of the first and/or second engaging member and limits relative movement between the first and second engaging members. In another embodiment, a guide member positioned on an outer surface of the detachable link limits relative movement.

Figure 1:
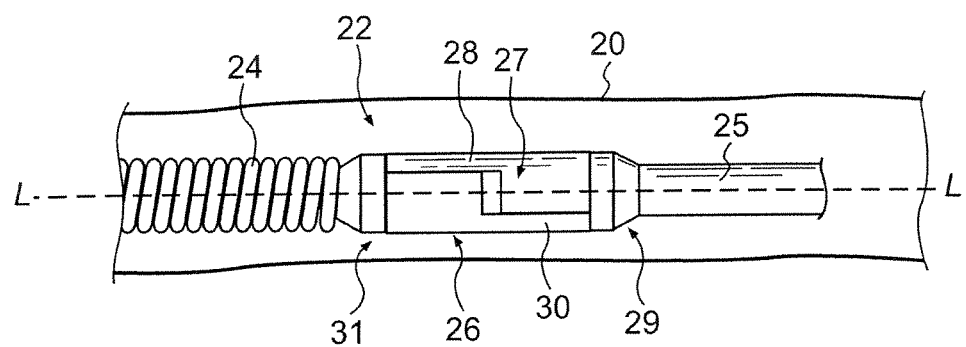
FIG. 1 is a cut-away view of a catheter illustrating one embodiment of the system described herein.
Figure 2A:
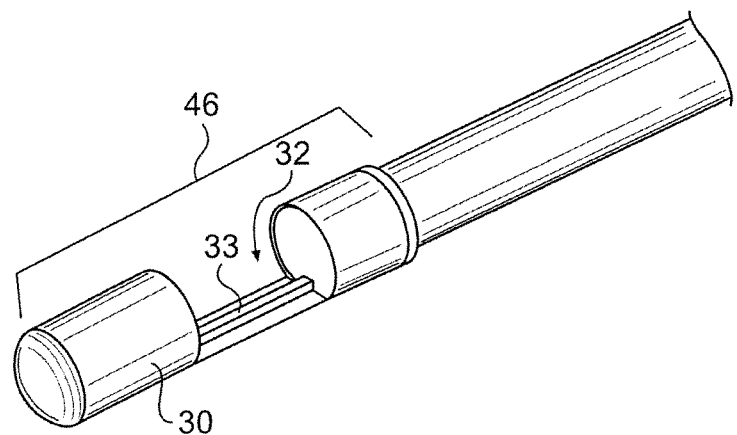
FIG. 2A is a perspective view of an engaging member used with the system of FIG. 1.

FIG. 1 shows a portion of catheter 20 cutaway to illustrate a system 22 for delivering an implantable device, in this case an embolic coil 24 (the terms "coil" and "embolic coil" are used interchangeably herein). The system includes a detachable link 26, for releasably joining the embolic coil 24 and a pusher wire 25, the detachable link comprising a first engaging member 28 and a second engaging member 30. System 22 further includes a guide member 32, as shown in FIGS. 2A and 2B, that inhibits premature detachment of engaging members 28, 30 during passage through catheter 20. In one embodiment, discussed below, guide member 32 is formed from an elongate protrusion 33 and a complimentary recess 35 that are adapted to mate with one another when engaging members 28, 30 are mated.

One skilled in the art will appreciate that the embolic coil 24 and pusher wire 25 are merely representative of the environment in which detachable link 26 operates, and that a variety of alternative medical devices could be substituted. For example, the systems described herein could be used to delivery a variety of implantable devices in addition, or as an alternative, to the embolic coil. Similarly, the pusher wire represents the variety of control devices for moving an implantable device through a lumen of a medical instrument. In addition, as disclosed in co-pending application Ser. No. 11/248,033, entitled "Multiple Interlocking Detachable Coils," filed Oct. 12, 2005, and incorporated by reference in its entirety, a second coil, or other such device, could be linked between pusher wire 25 and coil 24 via additional detachable links. Still further, while coil delivery system 22 is generally described with respect to the detachable link traveling through a catheter, one skilled in the art will appreciate that detachable link 26 may travel through a variety of medical instruments, such as, for example, introducers, and that the methods and devices describe herein are equally applicable to any medical device having a lumen for the delivery of a detachable, implantable device. In particular, the term "catheter" as used herein can refer to the variety of medical devices having an inner lumen adapted for receiving a medical instrument and/or implantable device.

As shown in FIGS. 1 through 2B, detachable link 26 generally includes a body 27 formed from at least engaging members 28, 30. Body 27 can have a generally elongate shape extending from a proximal portion 29 to a distal portion 31 along a longitudinal axis L. In one aspect, proximal and distal portions 29, 31 of body 27 can be integrally formed with coil 24 and pusher wire 25. Alternatively, body 27 can be fixedly mated with the coil and pusher wire. For example, the coil and pusher wire can be welded, adhered, and/or mechanically mated with body 27.

In one aspect, body 27 of detachable link 26 has a cylindrical outer surface that corresponds to an inner lumen of a catheter. However, both catheter and detachable link could have a variety of different shapes including rectangular, oval, D-shaped, triangular, and/or irregular. In addition, the catheter and detachable link could have different shapes from one another.

Body 27, and particularly engaging members 28, 30, can have a variety shapes and/or sizes that provide a detachable connection that self detaches after exiting the distal end of a catheter. In one aspect, engaging members 28, 30 can mechanically interlock with one another. For example, the engaging members can be configured as interlocking arms that are held together by catheter 20.

FIG. 3A illustrates a partially transparent view of catheter 20 containing an exemplary detachable link 26 in the "locked" position. During passage through catheter 20, inner surface 34 of catheter 20 can prevent detachable link 26 from "unlocking." For example, the diameter/width of the detachable link can closely match the internal diameter of the catheter such that detachable link 26 does not have sufficient room to detach within catheter 20. However, as shown in FIG. 3B, once detachable link 26 reaches the distal end 36 of catheter 20, detachable link 26 is no longer constrained by catheter 20 and can open to allow delivery of coil 24.

Figure 4B:
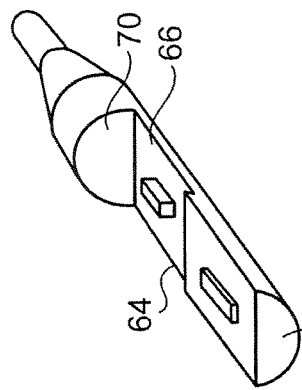
FIG. 4B is a perspective view of the engaging member of FIG. 4A.
Figure 4A:
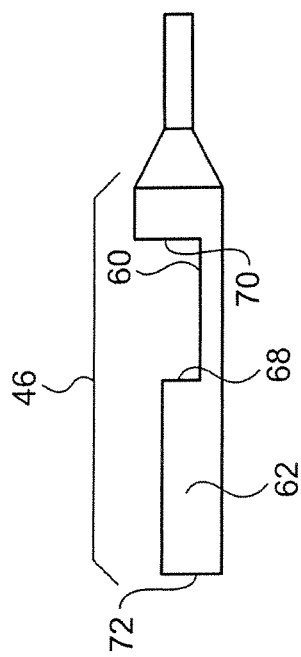
FIG. 4A is a side view of an embodiment of an engaging member described herein.

In one embodiment, the engaging members are generally configured such that opposed mating surfaces 46, 48 (FIGS. 2A and 2B) of the engaging members 28, 30 reversibly accept a portion of the adjacent engaging member 28, 30. The mating surfaces 46, 48 of the engaging members can be configured to transmit longitudinal forces (i.e., pushing/pull) so that a user can move coil 24 through catheter 20. FIGS. 4A and 4B illustrate an exemplary engaging member (e.g., engaging member 28) having a mating surface 46 comprising a receiving area 60 and an extension portion 62. In the illustrated embodiment, receiving area 60 has open sides 64, 66 and is bounded by end surfaces 68, 70.

Figure 5B:
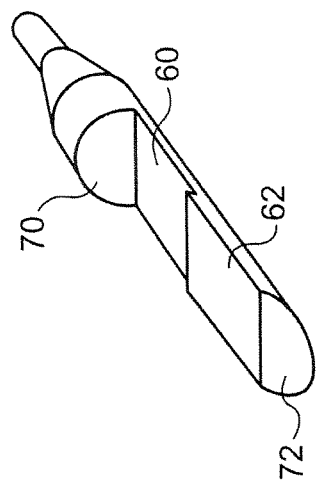
FIG. 5B is a perspective view of the engaging member of FIG. 5A.
Figure 5A:
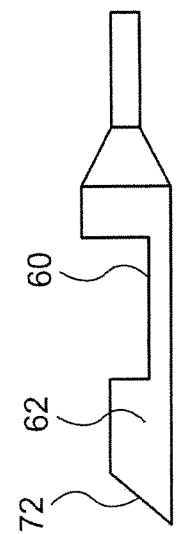
FIG. 5A is a side view of another embodiment of an engaging member described herein.

In one aspect, vertical surfaces (i.e., surfaces transverse to the longitudinal axis of the detachable link) of receiving area 60 and extension portion 62 allow coupled engaging members 28, 30 to push/pull one another. For example, end surface 68 can provide a vertical contact area for pulling on a similar vertical surface on an adjacent engaging member (e.g., engaging member 30). When engaging member 28 is pushed, end surface 70 can be pushed by a surface (e.g., surface 72) on an adjacent engaging member. While surfaces 68, 70, and 72 are illustrated as vertical, in another embodiment, illustrated in FIGS. 5A and 5B, at least one of the surfaces of engaging members can have a ramped configuration. In addition, while surfaces 68, 70, 72 are illustrated as planar, one or more of the surfaces could have a non-planar configuration such that receiving area 60 and extension portion 62 have a non-rectangular shape. One skilled in the art will appreciate that extension portion 62 and receiving area 60 can have a variety of shapes including, for example, a circular, oval, rectangular, multi-sided, or irregular shapes that are adapted to mate with receiving areas and protrusions of a corresponding, or different, shape.

In one embodiment, mating surfaces 46, 48 allow pushing/pulling of coil through catheter, but do not prevent relative movement between engaging members 28, 30 such that surfaces 46, 48 can move away from one another and/or rotate relative to one another. FIG. 6 illustrates a cross-section of detachable link 26 with engaging members 28, 30 partially separated from one another. As shown, the mating surfaces 46, 48, when engaged, cannot move toward one another, but receiving area 60 and extension portion 62 do not prevent movement of engaging member 28 away from engaging member 30 in a radial direction (i.e., in the direction indicated by angle α). Similarly, receiving area 60 and extension portion 62 do not prevent engaging members 28, 30 from pivoting or rotating relative to one another (e.g., pivoting on a longitudinal axis, such as longitudinal axis $l_1$).

Generally, the inner walls of catheter 20 will prevent the engaging members from separating from one another during transit though the catheter. However, where necessary, guide member 32 provides additional reinforcement to detachable link 26. For example, when the detachable link moves from an introducer to a catheter the interface may allow the detachable link additional room for movement. Guide member 32 reduces the freedom movement between engaging members 28, 30 so detachable link 26 will not prematurely detach or jam.

Figure 7A:
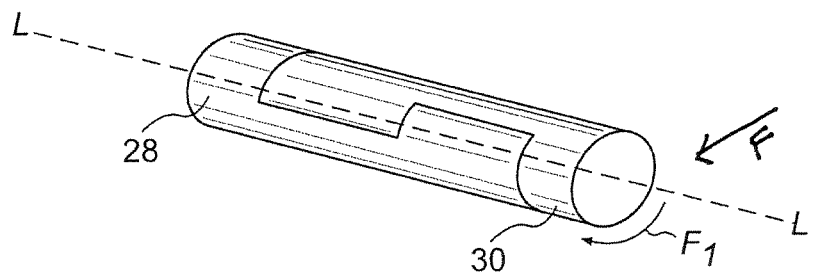
FIG. 7A is a perspective view of another embodiment of the detachable link described herein.
Figure 7B:
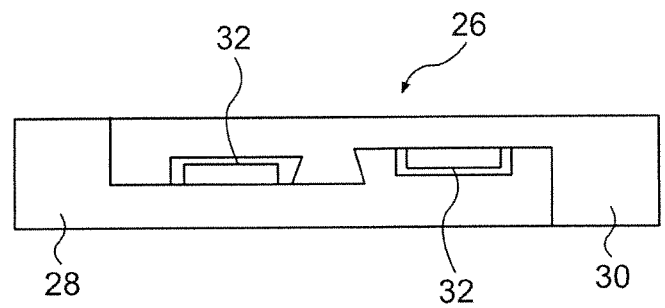
FIG. 7B is a side view of the detachable link of FIG. 7A.

In one embodiment, guide member 32 can prevent relative movement of engaging members 28, 30 caused by lateral and/or rotational forces on detachable link 26. FIG. 7A illustrates force F applied at an angle perpendicular to the longitudinal axis L of link 26. Force F, without the resistance of guide member 32 would move engaging member 30 transversely to longitudinal axis L and separate engaging members 28, 30. Guide members 32, as shown in a cross sectional view in FIG. 7B, act to prevent relative movement between engaging members transverse to a longitudinal axis. Similarly, a rotational force $F_1$, acting around a longitudinal axis of the detachable link would tend to cause engaging member 30 to pivot relative to engaging member 28. Guide member 32 can, in one embodiment, reinforce detachable link 26 against such rotational forces and prevent relative rotational movement between engaging members 28, 30.

In one embodiment, guide member 32 reduces the freedom of movement between engaging members 28, 30 by at least one degree. For example, guide members 32 can limit relative transverse movement, in at least one direction, between engaging members 28, 30. In another embodiment, the guide member can limit relative movement between the first and second engaging members 28, 30 by more than one degree of freedom. In one aspect, guide member 32 can limit, in one direction, transverse movement relative to a longitudinal axis of detachable link 26 and can limit relative rotational movement around at least one axis.

In addition, if engaging members 28, 30 partially separate, guide members 32 can prevent full separation (detachment) and/or jamming. Thus, the guide member or guide members can be particularly helpful where the diameter of the catheter through which detachable link 26 is traveling is larger than the diameter of the detachable link. Such variations in lumen diameter can occur where the catheter size is not closely matched to the implant delivery system and/or where the detachable link travels through an interface between the catheter and another device (e.g., between a catheter and an introducer).

Figure 8:
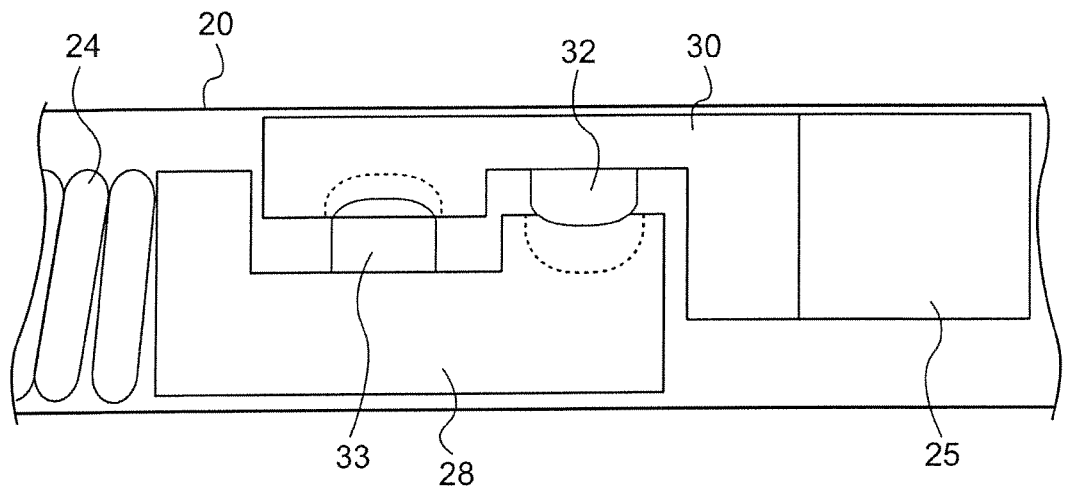
FIG. 8 is a cut-away view of a catheter illustrating an embodiment of the detachable link described herein in a partially separated configuration.

For example, in FIG. 8 guide member 32 is formed from elongate protrusion 33 and recess 35. As shown, elongate protrusions 33 extend partially into recesses 35 even through engaging members 28, 30 have partially separated. While engaging members 28, 30 are partially separated, guide members 32 limits at least some relative movement between the engaging members. The height of protrusions 33 should be greater than the difference between the width of detachable link 26 (when fully engaged) and the diameter of catheter 20, so that engaging members 28, 30 are constrained by guide members 32 and cannot fully detach. In addition, guide member 32 can prevent partially separated engaging member 30 from sliding over and jamming engaging member 28. In one aspect, guide members 32 inhibits axial, rotational, and/or pivotal movement between partially separated engaging members.

As mentioned above, guide member 32 can have a variety of configurations adapted to counter forces applied on detachable link 26. In one embodiment, the guide member comprises a protrusion and a corresponding recess. The protrusion can be generally elongate and positioned to counter relative transverse and/or rotational movement of the engaging members. In one aspect, the protrusion extends along an axis parallel to the longitudinal axis of the detachable link. FIG. 9A illustrates a partial view of an engaging member (e.g., engaging member 30) with a protrusion 33 extending along a longitudinal axis. Protrusion 33 can mate with a corresponding elongate recess (not shown) on an adjacent engaging member. In another embodiment, multiple protrusions can extend from the surface of engaging members 28 and/or engaging member 30. For example, FIGS. 9B and 9C illustrate multiple protrusions extending across mating surfaces of the engaging members.

In another embodiment, instead of an elongate protrusion, multiple protrusions can work together to prevent relative rotational and/or transverse movement. For example, guide member 32 can include a series of protrusions positioned next to each other such that the protrusions together extend at least some distance longitudinally. FIG. 9D illustrates a series of semi-spherical protrusions that can be received in a series of recesses and work together to prevent transverse relative movement of engaging members 28, 30. In addition, one recess can receive more than one protrusion. For example, the protrusions of FIG. 9D can all be received in the same recess.

In yet another embodiment, protrusion 33 can extend at an angle with respect to a longitudinal axis and/or extend transversely. FIG. 9E illustrates protrusion 33 extending at a angle with respect to the longitudinal axis of the engaging member. In addition, while the illustrated protrusion (protrusions) have a generally elongate configuration the protrusion can be a variety of shapes that reduce the freedom of movement between engaging members 28, 30.

For example, the protrusion and recess can have a variety of shapes and sizes including for example, spherical, oval, rectangular, triangular, and/or irregularly shaped. The configuration of protrusion 33 and recess 35 can be chosen depending on the desired limitation in relative movement between engaging members 28, 30. A shorter (height) protrusion and/or a wider recess (compared to the width of the protrusion) can limit transverse movement of the engaging members in at least one direction (can remove one degree of freedom) without limiting the ability of engaging members 28, 30 to pivot relative to one another. Conversely, a taller protrusion/deeper recess and a tighter fit between the protrusion and recess can limit relative transverse and/or rotational movement between the engaging members. In addition, the height of the protrusion and the depth of the recess can be chosen based on the amount of separation which the engagement members must reach before they can move relative to one another and thus detach or jam. One skilled in the art will appreciate that the size and shape of the protrusion and recess can be configured depending on the need to limit relative movement between the engaging members and/or on the anticipated dimensions of the lumen through which the system will travel.

In one embodiment, the protrusion and recess are adapted to mechanically mate without frictionally engaging. The mechanical engagement can counter relative translational and/or rotational movement while not inhibiting detachment. For example, the protrusion can have a smaller cross section than the recess such that the protrusion and recess can mate mechanically but not frictionally.

Protrusion 33 and/or recess 35 can be positioned on any of the mating surfaces of engaging members 28, 30. In one embodiment, protrusion 33 is positioned within recessed area 60. For example, protrusion 33 can be located on end surfaces 68, 70, on sides 64, 66 (where sides 64, 66 are enclosed), and/or a contact surface 74 of the recessed area 60. The recess 35, conversely, can be positioned on a surface of extension portion 62 which mates with recessed area 60. Alternatively, or additionally, protrusions 33 can be positioned on at least one of the surfaces of extension portion 62, such as, for example, end surface 72 or contact surface 76.

In another embodiment, each of engaging members 28, 30 includes a protrusion 33 and a recess 35 positioned on a surface generally parallel to the direction of travel of the detachable link. For example, each of engaging members 28, 30 can include a protrusion 33 positioned within recessed area 60 on a generally horizontal contact surface 74. Engaging members 28, 30 can also include recesses 35 positioned on horizontal top contact surface 76 of extension portion 62.

Figure 10A:
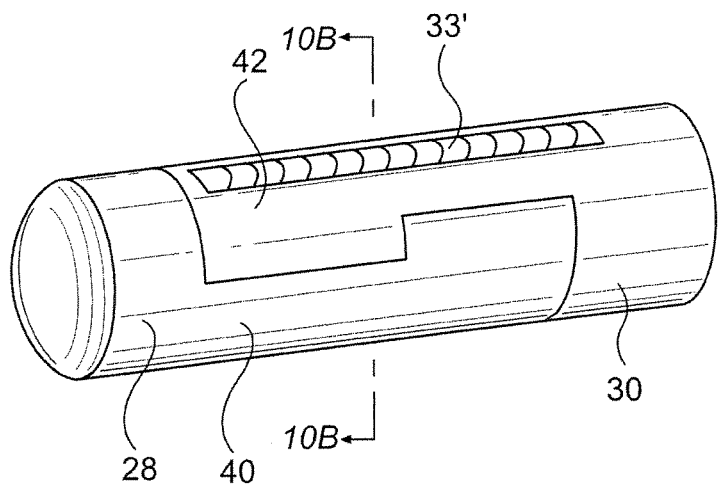
FIG. 10A is a perspective view of an embodiment of the detachable link described herein.
Figure 10B:
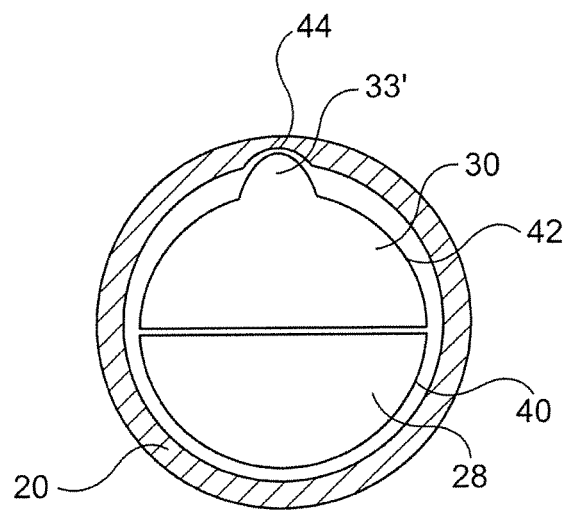
FIG. 10B is a cross-sectional view of the detachable link of FIG. 10A along the line B-B.

In another embodiment, the guide member can extend from an outer surface of the detachable link. For example, as shown in FIGS. 10A and 10B a protrusion 33' can extend from at least one of outer surfaces 40, 42 of engaging members 28, 30 and mate with a portion of the inner surface 34 of the catheter. In one aspect, the catheter can include a longitudinally extending feature that corresponds to protrusion 33' such that the engaging member from which protrusion 33' extends is inhibited from rotational and/or pivotal movement with respect to the catheter. For example, the catheter could include a channel 44 that corresponds to protrusion 33'. In use, protrusion 33' and channel 44 can keep elongate member 30 in line with the path of the catheter as the elongate member is pushed through the catheter. The guide member can thereby reduce the influence of transverse and/or rotational forces on engaging member 30 and help to prevent premature detachment of the detachable link. In another aspect, both engaging members 28, 30 can include a recess on an outer surface that corresponds to a feature on the inner surface of the catheter.

Engaging members 28, 30 and guide member 32 can be made from the variety of biocompatible materials. In one embodiment, the protrusion can be made of the same material as the engaging members. For example, the mating features and guide member can be machined from a single piece of stainless steel and/or platinum. Alternatively, the protrusion can be mated to the engaging members. One skilled in the art will appreciate that there are a variety of ways to fix protrusions to engaging member 28, 30, including, for example, welding, adhering, and/or mechanically connecting.

In one embodiment, system 22 can include materials to help determine the position of detachable link 26. In use, a surgeon may wish to know the location of the detachable link relative to the distal end of the catheter and/or relative to an anatomical location (e.g., target delivery location). To aid with visualization, at least a portion of system 22 can be constructed with materials which highlight detachable link 26 during an imaging procedure. For example, a portion of engaging members 28 and/or 30 can be formed from radio opaque material. One skilled in the art will appreciate that a variety of imaging capable materials can be used, including, for example, materials detectable with, x-ray, MRI, CT, PET, SPECT, fluoroscopy, and combinations thereof. Alternatively, or additionally, the detachable link can provide a user with tactile feedback to assist with determination of the location of the coil and/or detachable link within the catheter. For example, a distal portion of the catheter lumen can include a surface feature that will cause increased resistance to movement of a portion of system 22 through the catheter. For example, a distal portion of catheter 20 can include a surface feature (e.g., ribs) and/or a different material (e.g., providing a different coefficient of friction). When the increased resistance is felt, the user will be alerted to the location of the detachable link and/or coil within the catheter.

Further provided herein is a method for delivering a detachable, implantable device. Prior to delivery into a catheter, system 22 is assembled by mating the first and second engaging members with one another. Also, where the detachable link is not fixedly mated with the coil and/or pusher wire, the detachable link needs to be attached to the coil and pusher wire. Generally, the system will be provided to the end user in a preassembled configuration. For example, system 22 can be preassembled and delivered to the user in an introducer. The user can then move coil and detachable link from the introducer into a catheter via the pusher wire. As mentioned above, guide member 32 can help to prevent detachment as the detachable link moves from the introducer to the catheter by limiting at least one degree of freedom of movement between engaging members 28, 30.

Once moved into the catheter, the user can actuate the pusher wire to move the coil toward the egress port of the catheter (e.g., the distal end of the catheter). To facilitate delivery to the target tissue area the delivery method can include the step of visualizing the relative location of the detachable link and the distal end of the catheter. For example, an imaging technique, such as x-ray, MRI, CT, PET, SPECT and combinations thereof, can be used to visualize the coil and/or detachable link.

As part of delivery, the user can extend the coil through the end of the catheter and determine if the coil is properly located. If not, the user can then draw the coil and/or detachable link back into the catheter. Since the guide member reduces the freedom of movement of the engaging members, the engaging members are less likely to completely detach until fully exiting the distal end of the catheter. As such, the user has more freedom to adjust the location of the coil prior to allowing the coil to fully detach. Once the coil is properly situated, the user can allow the engaging members to fully detach and can withdraw the pusher wire and associated engaging member.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An implant delivery system, comprising:
   a detachable link connecting an implantable device to a pusher wire, the detachable link comprising an elongate body extending along a longitudinal axis from a proximal end to a distal end, the elongate body comprising:
   a first arm having a first slot and a first arm extension portion distal to the first slot, and
   a second arm having a second arm extension portion adapted to mate with the first slot, and a recessed area proximal of the second arm extension portion, the recessed area comprising a guide protrusion configured to mate with a guide recess located on the first arm extension portion when the second arm extension portion mates with the first slot to thereby inhibit relative transverse motion and/or rotational movement between the first and second arms when the first and second arms are mated,
   wherein the guide protrusion extends a full length of the recessed area of the second arm and the guide recess extends a full length of the first arm extension portion, and
   wherein the guide protrusion extends through less than a full width of the first arm extension portion when mated with the guide recess.

2. The system of claim 1, wherein the first slot extends transversely to the elongate body.

3. The system of claim 1, wherein the first slot extends a full width of the elongate body.

4. The system of claim 1, wherein the respective guide protrusion and guide recess are adapted to limit transverse movement of the second arm extension portion within the first slot when the first and second arms are mated.

5. The system of claim 1, wherein the respective guide protrusion and guide recess limit the relative movement between the first and second arms by at least one degree of freedom when the first and second arms are mated.

6. The system of claim 1, wherein the first slot and the second arm extension portion limit relative longitudinal movement of the first and second arms when the first and second arms are mated, and the respective guide protrusion and guide recess limits relative transverse movement of the first and second arms when the first and second arms are mated.

7. The system of claim 1, wherein the shape of the guide protrusion is configured to mate with the shape of the guide recess.

8. The system of claim 1, further comprising a delivery catheter defining an axial lumen, and having an open distal end.

9. The system of claim 8, wherein the first and second arms are slidably disposed within the lumen of the catheter, and are configured to self-detach when deployed out of the distal end of the catheter.

10. The system of claim 1, wherein the shape of the second arm extension portion is configured to mate with the shape of the first slot.

11. An implant delivery system, comprising:
    a delivery catheter defining an axial lumen and an open distal end in communication with the lumen;
    an implantable device; and a pusher wire coupled to the implantable device via a detachable link, wherein the implantable device and pusher wire are slidably disposed within the lumen of the catheter, the detachable link comprising a longitudinally extending body comprising first and second engaging members;

the first engaging member having a slot, and a first engaging member extension portion distal to the slot, the second engaging member having a second engaging member extension portion adapted to engage the first engaging member slot, and a recessed area proximal of the second engaging member extension portion, the recessed area comprising a guide protrusion configured to engage a guide recess located on the first engaging member extension portion when the second engaging member extension portion engages with the first engaging member slot to thereby inhibit relative transverse and/or rotational movement between the first and second engaging members when the first and second engaging members are engaged, wherein the guide protrusion extends a full length of the recessed area of the second engaging member and the guide recess extends a full length of the first engaging member extension portion, wherein the guide protrusion extends through less than a full width of the first engaging member extension portion when mated with the guide recess, and wherein the first and second engaging members self-detach when deployed out of the distal end of the catheter.

12. The system of claim 11, wherein the guide protrusion has an elongate shape.

13. The system of claim 11, further comprising at least one additional guide protrusion and at least one additional guide recess.

14. The system of claim 13, wherein the at least one additional guide protrusion extends from the slot of the first engaging member, and is configured to engage the at least one additional guide recess located on the extension portion of the second engaging member.

15. The system of claim 11, wherein the first and second engaging members are detachably coupled.

16. The system of claim 11, wherein the first engaging member extension portion and the recessed area of the second engaging member transmit longitudinal forces.

17. The system of claim 11, wherein the guide protrusion of the second engaging member recessed area and the guide recess of the first engaging member extension portion transmit at least some non-longitudinally directed forces between the first and second engaging members.

18. The system of claim 17, wherein the guide protrusion and guide recess transmit forces transverse to the longitudinal extending body of the detachable link.

19. The system of claim 11, wherein the respective guide protrusion and guide recess limit the relative movement between the first and second engaging members by at least one degree of freedom when the first and second engaging members are engaged.

* * * * *